(12) United States Patent
Beeley et al.

(10) Patent No.: US 8,821,457 B2
(45) Date of Patent: Sep. 2, 2014

(54) PUNCTAL PLUG CONTAINING DRUG FORMULATION

(75) Inventors: Nathan R. F. Beeley, Santa Barbara, CA (US); Bret A. Coldren, Vista, CA (US); Victor Lust, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/197,258

(22) Filed: Aug. 3, 2011

(65) Prior Publication Data

US 2012/0059338 A1    Mar. 8, 2012

Related U.S. Application Data

(60) Provisional application No. 61/380,737, filed on Sep. 8, 2010.

(51) Int. Cl.

| | |
|---|---|
| *A61F 2/02* | (2006.01) |
| *A61F 9/007* | (2006.01) |
| *A61F 9/00* | (2006.01) |
| *A61K 9/00* | (2006.01) |
| *A61M 31/00* | (2006.01) |

(52) U.S. Cl.
CPC ........... *A61F 9/00772* (2013.01); *A61F 9/0017* (2013.01); *A61K 9/0051* (2013.01); *A61M 31/002* (2013.01)
USPC .......................................... 604/294; 424/427

(58) Field of Classification Search
CPC ........................................................ A61F 2/02
USPC ........................................ 604/294; 424/427
See application file for complete search history.

(56) References Cited

U.S. PATENT DOCUMENTS

| | | | |
|---|---|---|---|
| 3,618,604 | A | 11/1971 | Ness |
| 3,626,940 | A | 12/1971 | Zaffaroni |
| 3,826,258 | A | 7/1974 | Abraham |
| 3,845,770 | A | 11/1974 | Theeuwes et al. |
| 3,962,414 | A | 6/1976 | Michaels |
| 3,993,071 | A | 11/1976 | Higuchi et al. |
| 4,014,335 | A | 3/1977 | Arnold |
| 4,923,699 | A | 5/1990 | Kaufman |
| 5,962,548 | A | 10/1999 | Vanderlaan et al. |
| 6,020,445 | A | 2/2000 | Vanderlaan et al. |
| 6,027,470 | A * | 2/2000 | Mendius ........................ 604/8 |
| 6,099,852 | A | 8/2000 | Jen |
| 6,196,993 | B1 | 3/2001 | Cohan et al. |
| 6,367,929 | B1 | 4/2002 | Maiden et al. |
| 6,822,016 | B2 | 11/2004 | McCabe et al. |
| 2007/0243230 | A1* | 10/2007 | de Juan et al. ................ 424/427 |
| 2009/0306608 | A1 | 12/2009 | Li et al. |

FOREIGN PATENT DOCUMENTS

| | | |
|---|---|---|
| EP | 0861659 B1 | 6/2011 |
| WO | WO 2009/137673 A1 | 11/2009 |

* cited by examiner

*Primary Examiner* — Leslie Deak
*Assistant Examiner* — Sara Sass
(74) *Attorney, Agent, or Firm* — Carl J. Evens

(57) ABSTRACT

Disclosed are lacrimal inserts and their method of use for delivery of medication to the eye. The plug includes a body portion sized to pass through a lacrimal punctum and be positioned within a lacrimal canaliculus of the eyelid. The plug may contain a core, or reservoir, at least partially within the body portion comprising a therapeutic agent that is configured to controlled release into the eye and is configured for release medication via a designated port, valve, or orifice in the insert housing and inhibits diffusion of medication via the housing itself.

3 Claims, 4 Drawing Sheets

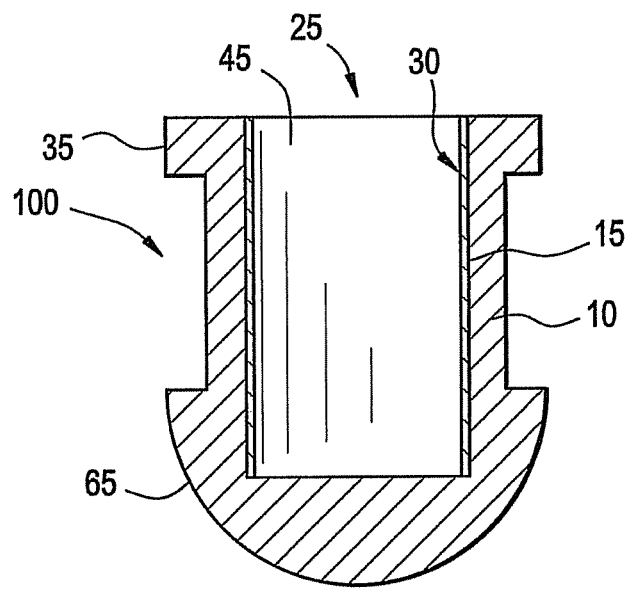
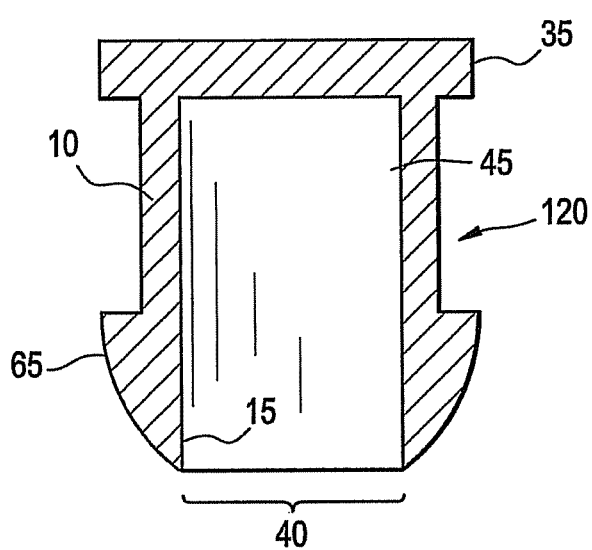
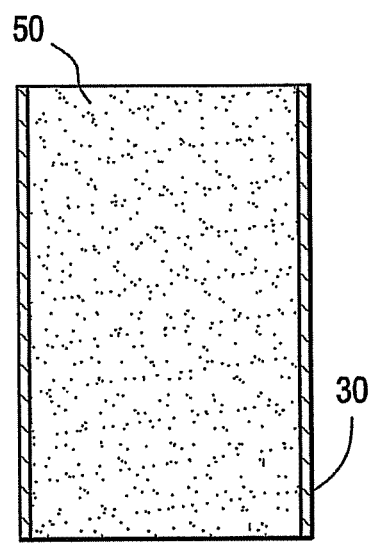

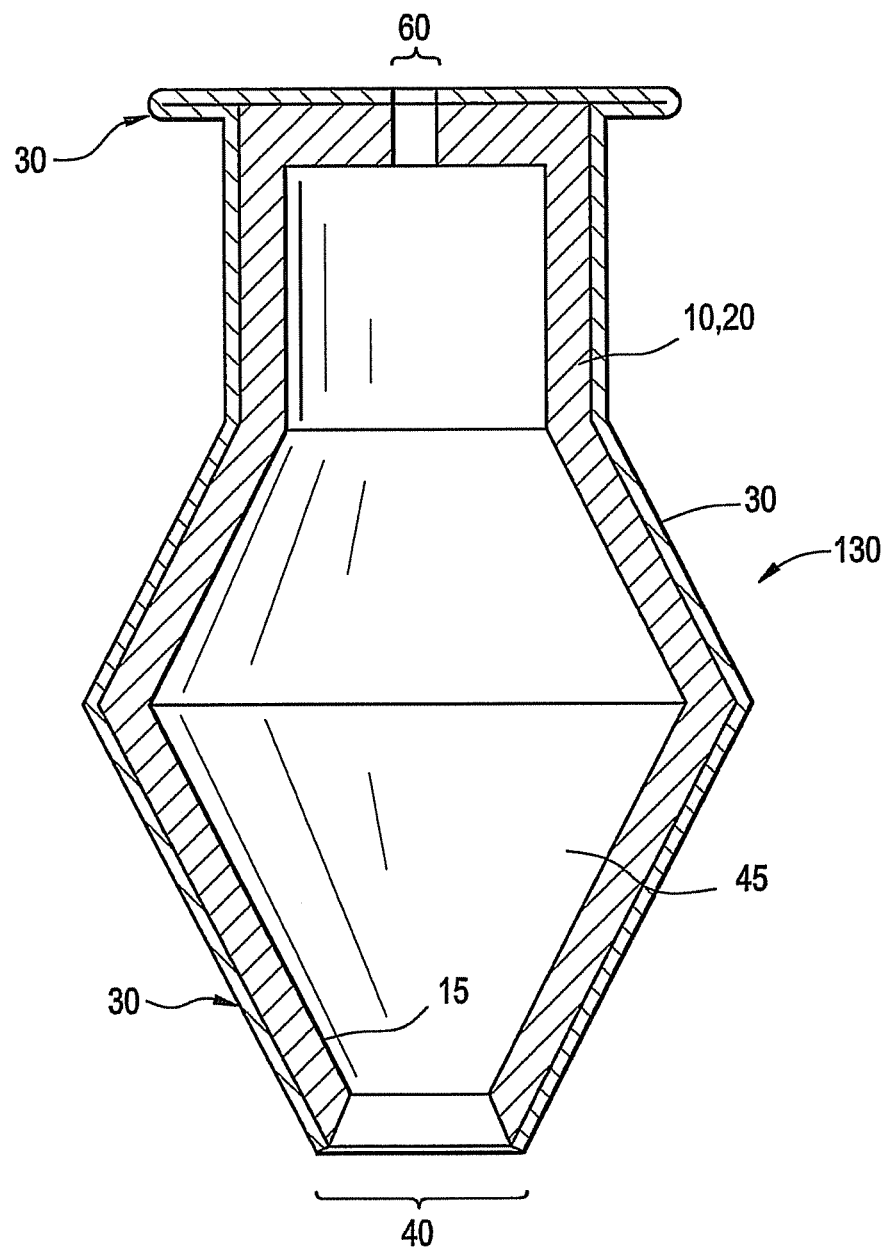

PUNCTAL PLUG CONTAINING DRUG FORMULATION

CROSS REFERENCE TO RELATED APPLICATIONS

This patent application claims the benefit of U.S. Provisional Patent Application Ser. No. 61/380,737 filed Sep. 8, 2010.

BACKGROUND OF THE INVENTION

1. Field of the Invention

The present invention relates to an ophthalmic insert and method for the release of medication to the eye for the treatment of eye disorders. More specifically, the present invention relates to punctal plugs sized to pass through a lacrimal punctum and be positioned within a lacrimal canaliculus of the eyelid and containing medication for controlled release into the eye.

2. Discussion of the Related Art

Active agents frequently are administered to the eye for the treatment of ocular diseases and disorders. Conventional means for delivering active agents to the eye involve topical application to the surface of the eye. The eye is uniquely suited to topical administration because, when properly constituted, topically applied active agents can penetrate through the cornea and rise to therapeutic concentration levels inside the eye. Active agents for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects and injections pose the risk of infection.

The majority of ocular active agents are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Therefore, sometimes one or more drops miss the eye. Older patients may have additional problems instilling drops due to arthritis, unsteadiness, and decreased vision, and pediatric and psychiatric patient populations pose difficulties as well.

It is known to use devices that may be inserted into one or more of an orifice of an individual's eye, such as a lacrimal punctum, to deliver active agents. One disadvantage of using such devices to deliver agents is that much of the agent may delivered in an initial, large bolus upon insertion of the device into the eye rather than a more linear delivery of the agent over time.

Prior topical sustained release systems include gradual release formulations, either in solution or ointment form, which are applied to the eye in the same manner as eye drops but less frequently. Such formulations are disclosed, for example, in U.S. Pat. No. 3,826,258 issued to Abraham and U.S. Pat. No. 4,923,699 issued to Kaufman. Due to their method of application, however, these formulations result in many of the same problems detailed above for conventional eye drops. In the case of ointment preparations, additional problems are encountered such as a blurring effect on vision and the discomfort of the sticky sensation caused by the thick ointment base.

Alternately, sustained release systems have been configured to be placed into the conjunctival cul-de-sac, between the lower lid and the eye. Such units typically contain a core drug-containing reservoir surrounded by a hydrophobic copolymer membrane which controls the diffusion of the drug. Examples of such devices are disclosed in U.S. Pat. No. 3,618,604 issued to Ness, U.S. Pat. No. 3,626,940 issued to Zaffaroni, U.S. Pat. No. 3,845,770 issued to Theeuwes et al., U.S. Pat. No. 3,962,414 issued to Michaels, U.S. Pat. No. 3,993,071 issued to Higuchi et al., and U.S. Pat. No. 4,014,335 issued to Arnold. However, due to their positioning, the units are uncomfortable and poor patient acceptance is again encountered.

SUMMARY OF THE INVENTION

The punctual plug containing a drug formulation of the present invention overcomes many of the disadvantages associated with the prior art.

In accordance with one aspect, the present invention is directed to a lacrimal insert. The lacrimal insert comprising a rounded or angled cross-sectional profile and the second end comprising one or more ribs, notches, protrusions, or generally annular features of greater width in cross-sectional profile than the generally straight housing wall, an inner surface wall defining a reservoir, and a drug core within the reservoir, wherein the drug comprises a therapeutic agent and the housing is comprises a material that inhibits the diffusion of the therapeutic agent through the housing walls.

In accordance with another aspect, the present invention is directed to a lacrimal insert. The lacrimal insert comprising a housing having a first end, a second end, and a housing wall therebetween, the first end comprising a rounded or angled cross-sectional profile and the second end comprising one or more ribs, notches, protrusions, or generally annular features of greater width in cross-sectional profile than the generally straight housing wall, an inner surface wall defining a reservoir, and a drug core within the reservoir, wherein the drug comprises a therapeutic agent and the housing is comprises a material that inhibits the diffusion of the therapeutic agent through the housing walls.

The present invention is directed to punctal plugs sized to pass through a lacrimal punctum and be positioned within a lacrimal canaliculis of the eyelid and which comprises one or more therapeutic agents for controlled release into the eye. The punctual plug is configured for easy insertion and long term stability. The plug is configured to hold the one or more therapeutic agents and release these one or more agents into the eye for treatment of a particular condition of the eye.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 3 is an illustrative example of a lacrimal insert, shown in cross-sectional view, that includes a barrier layer disposed on the interior surface of the housing and encompassing the interior portion of the reservoir in the lacrimal insert in accordance with the present invention.

FIG. 4A illustratively depicts a cross-sectional view of an inverted configuration for a lacrimal insert in accordance with the present invention.

FIG. 4B illustratively depicts a cross-sectional view of a drug core insert configured for deployment in a lacrimal insert in accordance with the present invention.

FIG. 5 depicts an exemplary inverted-design for a diamond-shaped lacrimal insert with a sealable loading port and exterior drug-impermeable barrier layer in accordance with the present invention.

DETAILED DESCRIPTION OF THE PREFERRED EMBODIMENTS

Figure 1:
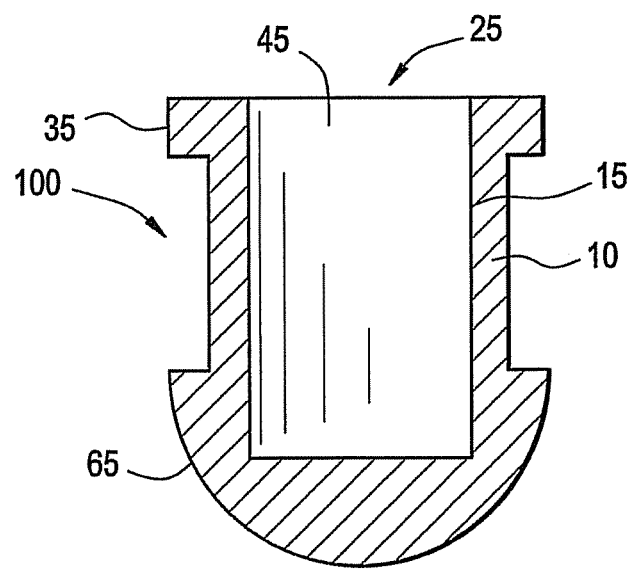
FIG. 1 is an illustrative example of a lacrimal insert, in cross-sectional view, having a housing comprising material into which an active, therapeutic agent may permeate in accordance with the present invention.

Punctal plugs have been in use for decades now to treat conditions of dry eye. More recently they have gained attention for use as drug delivery systems for the treatment of ocular diseases and conditions. Several challenges exist with formulating a drug to release at the desired daily rate and/or dose that will give efficacy while limiting adverse events.

Diffusion based drug delivery systems are characterized by a release rate of drug is dependent on its diffusion through an inert water insoluble membrane barrier. There are basically two diffusion designs; namely, reservoir devices and matrix devices. Reservoir devices are those in which a core of drug is surrounded by polymeric membrane. The nature of and/or the composition of the membrane determines the rate of release of drug from system. The process of diffusion is generally described by a series of equations governed by Fick's first law of diffusion. A matrix device consists of drug dispersed homogenously throughout a polymer.

Reservoir and matrix drug delivery systems are considered diffusion based sustained release systems and constitute any dosage form that provides medication over an extended period of time. The goal of a sustained release system is to maintain therapeutic levels of drug for an extended time period and this is usually accomplished by attempting to obtain zero-order release from the sustained release system. Sustained release systems generally do not attain this type of release profile but try to approximate it by releasing in a slow first order manner. Over time, the drug release rate from reservoir and matrix sustained release systems will decay and become non therapeutic.

Zero-order drug release constitutes drug release from a drug delivery system at a steady sustained drug release rate, that is, the amount of drug that is released from the drug delivery system over equal time intervals does not decay and remains at the therapeutic level. This "steady sustained release drug delivery system" is referred to as a zero-order drug delivery system and has the potential to provide actual therapeutic control by its controlled release.

Another drug release profile is referred to as pulsatile drug delivery. Pulsatile drug delivery is intended to release a therapeutic amount of a therapeutic agent at regular intervals.

Without regard to the desired drug release profile of the lacrimal insert device, the different therapeutic agents that are desirable for use in a lacrimal insert may react or behave differently from one another. Some therapeutic agents may be soluble in, effuse through, or react with various materials that may be used to construct the punctal plug (a term that may be used interchangeably throughout this specification with the term lacrimal insert).

It has been found that with certain therapeutic agents, it may be desirable to create a barrier layer between an active agent containing material contained in a reservoir within the lacrimal insert and the interior surface of the housing that defines the reservoir. Moreover, it has been found that retention of the drug core may be aided by selection of the geometric configuration of the lacrimal insert, as well as retention of the insert in the lacrimal puncta. Alternately, these features may be used alone or in combination, or varied. For example, the barrier layer may be disposed on the external surface of the punctal plug to inhibit diffusion of the therapeutic agent via the housing of the puntal plug and to inhibit the infusion of lacrimal fluid into the reservoir holding the active agent containing material.

To illustrate these concepts with greater specificity, we now turn to the drawings. These drawings are meant to be instructive, but not exhaustive of the possible structure and materials of the exemplary embodiments of the present invention and wherein similar reference numerals refer to similar structure.

An exemplary device illustrative of a punctal plug configured for release of a therapeutic agent is shown in FIG. 1. Shown is punctal plug 100 having a rounded "arrowhead" like first end 65 designed to permit insertion of the device into a lacrimal punctum of a patient. The punctal plug 100 has a housing 10 and a second end having a flange (or lip) 35 that may engage the surface of the eye and inhibit the punctal plug 100 from being completely inserted into the lacrimal punctum. The punctal plug 100 has an interior cavity, or reservoir, configured to contain a quantity of therapeutic agent or agent that is contained in a carrier or other material, generally referred to herein as an active-agent containing material. The reservoir is defined by the interior surface of the housing 15.

Figure 2:
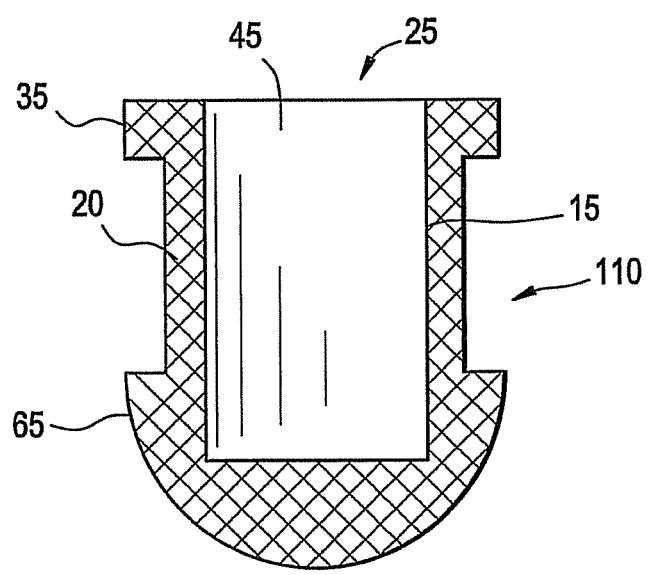
FIG. 2 is an illustrative example of a lacrimal insert, in cross-sectional view, having a housing comprising material that is substantially impermeable by an active, therapeutic agent contained within the reservoir of the lacrimal insert in accordance with the present invention.

FIG. 2 illustrates an alternate exemplary embodiment of the punctal plug 100 shown in FIG. 1 as punctal plug 110 which has a housing 20 that comprises a material that is impermeable or substantially impermeable to a therapeutic agent or active-agent containing material contained in the reservoir 45.

FIG. 3 shows punctal plug 100 having a barrier layer 30 disposed on the interior surface 15 of the housing 10 that defines that reservoir 45. The barrier layer 30 may be applied in situ as a coating or may be prepared and inserted into the punctal plug 100 prior to the insertion of the therapeutic agent or active-agent containing material in the reservoir 45 via an opening 25.

FIG. 4A shows an inverted configuration for a punctal plug 120 having an opening 40 in the tapered or "arrow head" portion of the insert 65 and a closed end having flanges 35 that inhibit over insertion of the punctal plug 120. An insert configured for deployment in a lacrimal insert, such as the various illustrated punctal plugs 100, 110, 120, 130, is shown in FIG. 4B. The insert has a barrier layer 30 for containing the therapeutic agent or active-agent containing material 50.

An inverted, diamond-shaped punctal plug 130 is illustrated in FIG. 5. This exemplary configuration for a lacrimal insert may have a housing that is permeable or impermeable to an active agent containing material disposed in the reservoir 45 and includes a barrier layer 30 on the exterior of the housing 10,20. An opening 40 in the arrowhead portion of the device is provided to facilitate loading of the therapeutic agent or active-agent containing material into the reservoir 45. A removable pore, diffusion membrane, or valve structure 60 may be provided to permit the release of therapeutic agent or active-agent containing material from the lacrimal insert 130 into the patient's lacrimal fluid. In this exemplary embodiment, the geometry chosen for the housing 10,20 of the lacrimal insert 130 improves the retention of the device in the lacrimal punctum while also aiding the retention of a drug core in the reservoir 45.

Figure 6:
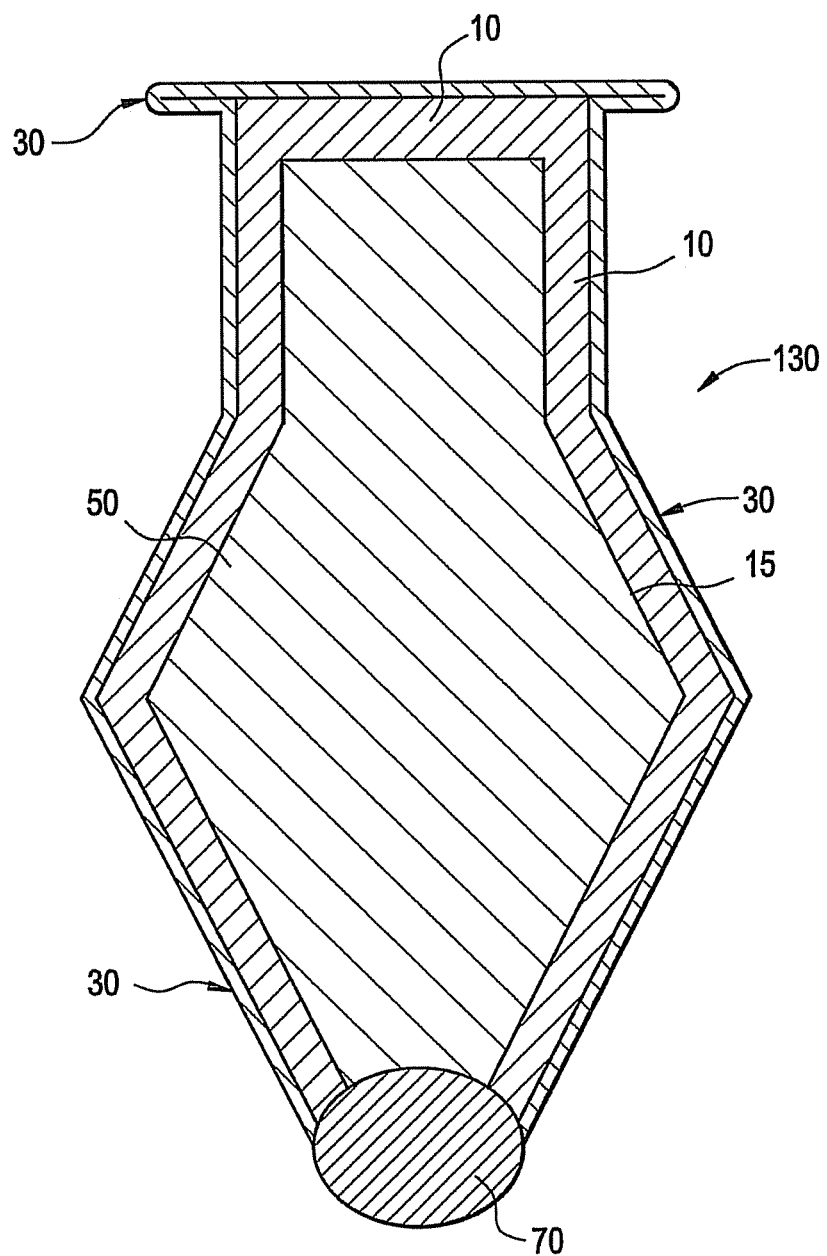
FIG. 6 depicts an exemplary inverted-design for a diamond-shaped lacrimal insert with a sealed loading port and exterior drug-impermeable barrier layer in accordance with the present invention.

FIG. 6 illustrates another exemplary embodiment of the invention on which the inverted, diamond-shaped housing has a drug core 50 comprising a therapeutic agent or active-agent containing material. The drug core 50 is loaded into the device via an orifice 70 that is then sealed using a sealant or overmold structure. The externally applied barrier layer 30 is configured to inhibit diffusion of the therapeutic agent or active-agent containing material through the surfaces of the lacrimal insert 130, except via the sealant or overmold structure disposed over orifice 70, thereby permitting the drug to enter the patient's lacrimal fluid via diffusion through the material sealing or molded over the orifice 70.

A punctal plug configuration according to an illustrative exemplary embodiment of the invention may provide for containment of solid, liquid, semi-solid, oil, suspension, particulate and gel formulations of a therapeutic agent or drug. Exemplary materials for construction of the punctal plug, barrier layer, or other components of the plug that are intended for inhibiting the diffusion or release of therapeutic agent or active-agent containing material, or are intended to inhibit the infusion of lacrimal fluid into the reservoir of the lacrimal insert by means other than orifices, ports, membranes, or valves included for the purpose of regulating the delivery of therapeutic agent or active ingredient may comprise Polytetrafluoroethylene, Fluorinatedethylenepropylene, Perfluoroalkoxy, Polyvinylidene Fluoride, Tetrafluoroethylene, Hexafluoropropylene and Vinylidene Fluoride, polyvinylidene chloride (Saran®), Ethylenetetrafluoroethylene, Chloro Trifluoro Ethylene/Ethylene Copolymer, Polyethylene Terepthalate Polyester, Polyetheretherketone, Nylon 6/6, Nylon 11, Nylon 12, Pebax, Polyethylene, Ultra high molecular weight polyethylene, Ultra low molecular weight polyethylene, High molecular weight polyethylene, High density polyethylene, High density cross-linked polyethylene, Cross-linked polyethylene, Medium density polyethylene, Low density polyethylene, Linear low density polyethylene, Very low density polyethylene, Polypropylene, Polycarbonate, Cyanoacrylate, Polyimide, Polyamide, Polysulfone, Polyetherimide, Polytheresulfone, Polyphenylene Sulfide, Polyphenylene Oxide, butyl rubber (bromobutyl rubber, chlorobutyl rubber), Ethylene Propylene Diene Monomer (Rubber), Zeonor, Zeonex, Parylene, Parylene N, Parylene C, Parylene D, Parylene AF-4, Parylene SF, Parylene HT, Parylene A, Parylene AM, Parylene VT-4, Parylene CF, and Parylene X, Polyvinyl chloride, Polyisobutylene, Fluro silicones, Liquid curable perfluoropolyether, polybutylene terephthalate, and Polystyrene. Also included are biodegradable material structures comprising polyesters of lactide, glycolide, and copolymers thereof; polyannhydrides of polysebacid acid, poly(carboxyphenoxyalkane) and copolymers thereof (for example polysebacic acid-co-carboxyphenoxypropane); polyhydroxybutyric acid, polydioxanone, A punctal plug configuration according to an illustrative exemplary embodiment of the invention may, in addition to providing for containment of solid, liquid, semi-solid, oil, suspension, particulate and/or gel formulations of a therapeutic agent or drug, may comprise a diffusion membrane to aid in the controlled release of therapeutic agent of active-agent containing material stored in the reservoir of the device. Materials for constructing such a structure may be selected from the following non-exhaustive list of illustrative compositions and comprise polyvinylacetate, polyethylene-co-vinylacetate (vinyl acetate levels >10 wt %), polyurethanes, polyvinyl alcohol, Eudragit® family of methacrylic copolymers including grades RS, RL, silicone rubber, styrene butadiene rubber, styrene-ethylene/butylenes-styrene block copolymers (Kraton® family of polymers and formulated/blended compositions thereof), polybutylmethacrylate, polyisobutylmethacrylate, polybutylacrylate, polyisobutylacrylate, cellulose and cellulose derivatives. Also included are biodegradable materials comprising polycaprolactone and copolymers thereof with polyethyleneglycol, polypropanediolcarbonate, polyorthoesters; polypropylene glycol-co-fumaric acid.

Generally, membranes diffuse water and/or drug through them, while "barriers" allow only insignificant quantities to pass (per application requirements and total area). Valve and pore structures use fluid passageways in direct connectivity with an external environment, and thus may be made from either membrane or barrier material. The barrier material is often preferred to avert the contribution of two release mechanisms (direct and diffusive). But sometimes when a valve/pore/actuator structure requires a material for mechanical function that happens to be drug-permeable, it is unavoidable that it may require an additional inner/outer barrier material.

MDPE (medium density polyethylene) is defined by a density range of 0.926-0.940 g/cm$^3$. MDPE may be produced by chromium/silica catalysts, Ziegler-Natta catalysts or metallocene catalysts. MDPE has good shock and drop resistance properties. It also is less notch sensitive than HDPE, and its stress cracking resistance is better than HDPE. MDPE is typically used in gas pipes and fittings, sacks, shrink film, packaging film, carrier bags and screw closures.

LLDPE (linear low density polyethylene) is defined by a density range of 0.915-0.925 g/cm$^3$. LLDPE is a substantially linear polymer with significant number of short branches, commonly made by the copolymerization of ethylene with short-chain alpha olefins (for example, 1-butene, 1-hexene and 1-octene). LLDPE has a higher tensile strength than LDPE, and it exhibits higher impact and puncture resistance than LDPE. Lower thickness (gauge) films may be blown, compared with LDPE, with better environmental stress cracking resistance, but it not as easy to process. LLDPE is used in packaging, particularly film for bags and sheets. Lower thickness LLDPE may be used compared to LDPE. Cable covering, toys, lids, buckets, containers and pipe utilize LLDPE. While other applications are available, LLDPE is used predominantly in film applications due to its toughness, flexibility and relative transparency.

LDPE (low density polyethylene) is defined by a density range of 0.910-0.940 g/cm$^3$. LDPE has a high degree of short and long chain branching, which means that the chains do not pack into the crystal structure as well. It has, therefore, less strong intermolecular forces as the instantaneous-dipole induced-dipole attraction is less. This results in a lower tensile strength and increased ductility. LDPE is created by free radical polymerization. The high degree of branching with long chains gives molten LDPE unique and desirable flow properties. LDPE is used for both rigid containers and plastic film application such as plastic bags and films wraps.

VLDPE (very low density polyethylene) is defined by a density range of 0.880-0.915 g/cm$^3$. VLDPE is a substantially linear polymer with high levels of short-chain branches, commonly made by copolymerization of ethylene with short-chain alpha-olefins (for example, 1-butene, 1-hexene and 1-octene). VLDPE is most commonly produced using metallocene catalysts due to the greater co-monomer incorporation exhibited by these catalysts. VLDPEs are used for hose and tubing, ice and frozen food bags, food packaging and stretch wrap as well as impact modifiers when blended with other polymers.

Recently much research activity has focused on the nature and distribution of long chain branches in polyethylene. In HDPE a relatively small number of these branches, perhaps 1 in 100 or 1,000 branches per backbone carbon, may significantly affect the rheological properties of the polymer.

As used herein, the term "active agent" refers to an agent capable of treating, inhibiting, or preventing a disorder or a disease. Exemplary active agents include, pharmaceuticals and nutraceuticals. Preferred active agents are capable of treating, inhibiting, or preventing a disorder or a disease of one or more of the eye, nose and throat.

As used herein, the term "punctal plug" refers to a device of a size and shape suitable for insertion into the inferior or superior lacrimal canaliculus of the eye through, respectively, the inferior or superior lacrimal punctum. Exemplary and illustrative devices are disclosed in U.S. Pat. No. 6,196,993 and U.S. Published Patent Application No. 20090306608A1, both of which are hereby incorporated by reference in their entireties.

As used herein, the term "opening" refers to an opening in the body of a device of the invention of a size and shape through which the active agent may pass. Preferably, only the active agent may pass through the opening. The opening may be covered with a membrane, mesh, grid or it may be uncovered. The membrane, mesh, or grid may be one or more of porous, semi-porous, permeable, semi-permeable, and biodegradable.

The devices of the present invention have a reservoir in which is found an active agent-containing material and an active agent therein. The active agent may be dispersed throughout the active agent-containing material or dissolved within the material. Alternatively, the active agent may be contained in inclusions, particulates, droplets, or micro-encapsulated within the material. Still as another alternative, the active agent may be covalently bonded to the material and released by hydrolysis, enzymatic degradation and the like. Yet as another alternative, the active agent may be in a reservoir within the material.

In an exemplary embodiment of the present invention, the active agent may be released in a controlled manner, meaning over a period of time by using an active agent-containing material in which the agent is present in a continuous concentration gradient throughout the material or by using a discontinuous concentration gradient. This is in contrast to a device that exhibits a "burst" or immediate release upon insertion of an amount of active agent that is greater than the average release rate over time. The structure recited herein, however, may be applied with equal success in devices designed to release the therapeutic agent or active-agent containing material according to either profile.

Without being bound to any particular theory, it is believed that an active agent-containing material that does not undergo significant chemical degradation during the time desired for the release of active agent will release the agent by diffusion through the matrix to a device's release surfaces, meaning surfaces of the active agent-containing material in contact with a person's body fluid. According to Fick's Law, the diffusive transport or flux, J, of the agent through the active agent-containing material is governed at each point and each time by the local concentration gradient, the diffusivity of the active agent with the material D, and the spatial variation of the cross-sectional geometry of the device.

The local gradient may be controlled by placing more active agent at one location in the active agent-containing material relative to another location. For example, the concentration profile may be a continuous gradient from one end of the material to the other. Alternately, the matrix may have a discontinuous gradient, meaning that one section of the material has a first concentration and the concentration abruptly changes to a second, different concentration in an adjacent section of the matrix, such as that illustrated in alternate exemplary embodiments in FIGS. 1 and 4 as being contained in the drug impermeable housing 40. The diffusivity for the active agent may also be spatially controlled by varying one or more of the chemical composition, porosity, and crystallinity of the active agent-containing material.

Additionally, the spatial variation of the material's cross-sectional geometry may be used to control diffusivity. For example, if the material was in the form of a straight rod that has a uniform active agent concentration, diffusivity will be reduced when the area at the open end of the material is significantly smaller than the average of the entire material. Preferably, the material area at the open end of the device is no more than one-half of the average cross sectional area of the material, meaning the cross section determined perpendicular to the primary dimension of active agent transport use.

One of ordinary skill in the art will recognize that, depending on how one varies one or more of the local concentration gradient, the diffusivity of the active agent from the material, and the spatial variation of the cross-sectional geometry of the device, a variety of release profiles may be obtained including, first order, second order, biphasic, pulsatile and the like. For example, either or both of the active agent concentration and diffusivity may increase from the surface to the center of the active agent-containing material in order to achieve more initial release. Alternately, either or both may be increased or decreased and then increased again within the material to achieve a pulsatile release profile. The ability to achieve a variety of release profiles by varying local concentration gradient, the diffusivity of the active agent, and the spatial variation of the cross-sectional geometry may eliminate the need for rate-limiting membranes in the device.

The exemplary devices of the present invention comprise a reservoir within the body, and the reservoir includes at least one active agent-containing material, as shown in an exemplary embodiments in FIGS. 1 and 2. The body 20 is preferably impermeable to the active agent, meaning only an insubstantial amount of active agent can pass there through, and the body has at least one opening 25 through which the active agent is released. An active agent-containing material useful in the devices of the present invention is any material that is capable of containing the active agent, does not alter the chemical characteristics of the active agent, and does not significantly chemically degrade or physically dissolve when placed in contact with ocular fluids. Preferably, the active agent-containing material is non-biodegradable, meaning that it does not degrade to a substantial degree upon exposure to biologically active substances typically present in mammals. Additionally, the active agent-containing material is capable of releasing the active agent by one or more of diffusion, degradation, or hydrolyzation. Preferably, the active agent-containing material is a polymeric material, meaning that it is a material made of one or more types of polymers.

When the active agent-containing material is combined with the active agent, thereby forming the material included in the reservoir 45, the material may also contain one or more materials that are insoluble in water and non-biodegradable, but from which the active agent can diffuse. For example, if the active agent-containing material is a polymeric material, the material may comprise of one or more polymers that are insoluble in water and non-biodegradable.

Suitable polymeric materials for the active agent-containing material include hydrophobic and hydrophilic absorbable and non-absorbable polymers. Suitable hydrophobic, non-absorbable polymers include, ethylene vinyl alcohol ("EVA"), fluorinated polymers including polytetrafluoroethylene ("PTFE") and polyvinylidene fluoride ("PVDF"), polypropylene, polyethylene, polyisobutylene, nylon, polyurethanes, polyacrylates and methacrylates, polyvinyl palmitate, polyvinyl stearates, polyvinyl myristate, cyanoacrylates, epoxies, silicones, copolymers thereof with hydrophobic or hydrophilic monomers, and blends thereof with hydrophilic or hydrophobic polymers and excipients.

Hydrophilic, non-absorbable polymers useful in the present invention include cross-linked poly(ethylene glycol), poly(ethylene oxide), poly(propylene glycol), poly(vinyl alcohol), poly(hydroxyethyl acrylate or methacrylate), poly(vinylpyrrolidone), polyacrylic acid, poly(ethyloxazoline), and poly(dimethyl acrylamide), copolymers thereof with hydrophobic or hydrophilic monomers, and blends thereof with hydrophilic or hydrophobic polymers and excipients.

Hydrophobic, absorbable polymers that may be used include aliphatic polyesters, polyesters derived from fatty acids, poly(amino acids), poly(ether-esters), poly(ester amides), polyalkylene oxalates, polyamides, poly(iminocarbonates), polycarbonates, polyorthoesteres, polyoxaesters, polyamidoesters, polyoxaesters containing amine groups, phosphoesters, poly)anhydrides), polypropylene fumarates, polyphosphazenes, and blends thereof. Examples of useful hydrophilic, absorbable polymers include polysaccharides and carbohydrates including, crosslinked alginate, hyaluronic acid, dextran, pectin, hydroxyethyl cellulose, hydroxy propyl cellulose, gellan gum, guar gum, keratin sulfate, chondroitin sulfate, dermatan sulfate, proteins including collagen, gelatin, fibrin, albumin and ovalbumin, and phospholipids including phosphoryl choline derivatives and polysulfobetains.

More preferably, the active agent-containing material is a polymeric material that is polycaprolactone. Still more preferably, the material is poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about fifty percent each of polycaprolactone and ethylene vinyl acetate is used.

The polymeric material used is preferably greater than about ninety-nine percent pure and the active agents are preferably greater than about ninety-seven percent pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded.

The release kinetics of the therapeutic agent or active-agent containing material may be controlled via spatial gradients of the properties of degradability and drug permeability of the active agent-containing material. For example, in those cases in which drug release kinetics are dominated by the rate of material degradation, a spatial degradation in the material chemistry including, polylactide-glycolide copolymers of differing monomer ratios, adjacent polyglycolide and polycaprolactone layers and the like, results in spatial gradients and varied release rates as the material degradation front moves through the device. By way of further example, a material may erode more slowly initially in a first, outer material, and more quickly in a second, inner material to achieve phased release kinetics.

In the case of a non-degradable material that elutes the active agent solely through diffusion-dominated mechanisms, spatial gradients in the material's permeability may control release kinetics beyond what is possible with a homogeneous material. In the diffusion-dominated mechanism, the material permeability controls release kinetics and is influenced by the material's porosity as well as the active agent solubility and diffusivity. By forming an active agent-loaded layer of an outer material with a higher permeability, the active agent elution may be controlled to be more linear with less burst effect than that which is otherwise achieved with a single, homogeneous, diffusion material.

The spatial gradients in biodegradability or permeability may be combined with continuous or step-wise gradients in the active agent loading profile. For example, a punctal plug material core having an outer segment loaded with a low active agent concentration and with a relatively low active agent permeability may be adjacent to an inner material segment loaded with a high agent concentration and with a relatively high active agent permeability, which combination achieves release kinetics unobtainable with a homogeneous material ad homogeneous active agent loading. The initial burst release is reduced and the release of the last active agent content is accelerated relative to a conventional homogeneous active agent loaded device.

Phase-separated inclusions may be used to control one or both of diffusive and degradative kinetics of the active agent-containing material. For example, water soluble polymers, water soluble salts, materials with a high diffusivity for the active agent and the like may be used as a destabilizing inclusion to enhance degradation or diffusion rates. When the hydrolysis front reaches an inclusion, the inclusion rapidly dissolves and increases porosity of the active agent-containing material. The inclusions may be incorporated as gradients or layers that allow additional tailoring of the release profile.

As another alternate, a percolated network of destabilizing inclusions may be used. When used in a non-biodegradable active agent-containing material, these inclusions form islands within the material that can possess high diffusivity for the active agent. Useful inclusions will have a higher diffusivity for the active agent than the active agent-containing material. Examples of such inclusions include, propylene glycol, silicone oil, immiscible dispersed solids such as a polymer or wax and the like. As yet another example, an inclusion that acts to adsorb water, swell the active agent-containing material and increase local diffusion kinetics may be used.

As still another alternate, stabilizing inclusions that have a low active agent diffusivity are used. These inclusions act to form a barrier that slows diffusive transport of the active agent in the vicinity of the inclusion. The overall effect is a reduction of active agent permeability in a base material that is otherwise the same. Example of such inclusions include, micro to nano-sized silicate particles dispersed through the base material of one or both of polycaprolactone and ethylenecovinylacetate homogeneously or in continuous step-wise gradients.

The present invention encompasses numerous devices for the delivery of active agents to the eye each having various features and advantages. For example, certain devices may have a body with a first end, a second end, and a lateral surface extending between the two ends. The lateral surface preferably has an outer diameter that is substantially circular in shape and, thus, the body preferably has a cylindrical shape. A portion of the lateral surface of certain of the devices preferably has an outer diameter that is greater than the outer diameter of the remainder of the lateral surface as shown in FIGS. 5, 6. The enlarged portion may be any size or shape, and may be present on any part of the lateral surface, in punctal plug embodiments, the enlarged portion is of a size so that it at least partially anchors the punctal plug in the lacrimal canaliculus and preferably, the enlarged portion is at one end of the plug. Further, it has been found that by selecting a cross-sectional profile geometry of this nature may improve the retention of the drug-containing core present in the reservoir. One ordinarily skilled in the art will recognize that any of a wide variety of shapes may be possible.

The body of the punctal plugs of the present invention may take any shape and size, preferably, the body is in the shape of an elongated cylinder. The body will be about 0.8 to about 5 mm in length, preferably about 1.2 to about 2.5 mm in length. The width of the body will be about 0.2 to about 3, preferably 0.3 to about 1.5 mm. The size of the opening will be from about 1 nm to about 2.5 mm and preferably about 0.15 mm to about 0.8 mm. Instead of one large opening at any one location, multiple small openings may be used. The body of the plug may be wholly or partially transparent or opaque. Optionally, the body may include a tint or pigment that makes the plug easier to see when it is placed in a punctum.

In addition to those already recited here, the body of the devices of the present invention may be made of any suitable biocompatible material including silicone, silicone blends, silicone co-polymers, such as, for example, hydrophilic monomers of polyhydroxyethylmethacrylate ("pHEMA"), polyethylene glycol, polyvinylpyrrolidone, and glycerol, and silicone hydrogel polymers such as, for example, those described in U.S. Pat. Nos. 5,962,548, 6,020,445, 6,099,852, 6,367,929, and 6,822,016, incorporated herein in their entireties by reference. Other suitable biocompatible materials include, for example: polyurethane; polymethylmethacrylate; poly(ethylene glycol); poly(ethylene oxide); poly(propylene glycol); poly(vinyl alcohol); poly(hydroxyethyl methacrylate); poly(vinylpyrrolidone) ("PVP"); polyacrylic acid; poly(ethyloxazoline); poly(dimethyl acrylamide); phospholipids, such as, for example, phosphoryl choline derivatives; polysulfobetains; acrylic esters, polysaccharides and carbohydrates, such as, for example, hyaluronic acid, dextran, hydroxyethyl cellulose, hydroxyl propyl cellulose, gellan gum, guar gum, heparan sulfate, chondroitin sulfate, heparin, and alginate; proteins such as, for example, gelatin, collagen, albumin, and ovalbumin; polyamino acids; fluorinated polymers, such as, for example, PTFE, PVDF, and teflon; polypropylene; polyethylene; nylon; and EVA.

The surface of the devices may be wholly or partially coated. The coating may provide one or more of lubriciousness to aid insertion, muco-adhesiveness to improve tissue compatibility, and texture to aid in anchoring the device. Examples of suitable coatings include gelatin, collagen, hydroxyethyl methacrylate, PVP, PEG, heparin, chondroitin sulphate, hyaluronic acid, synthetic and natural proteins, and polysaccharides, thiomers, thiolated derivatives of polyacrylic acid and chitosan, polyacrylic acid, carboxymethyl cellulose and the like and combinations thereof.

Certain exemplary embodiments of the devices of the present invention have a body made of a flexible material that conforms to the shape of whatever it contacts. Optionally, in the punctal plug embodiment, there may be a collarette formed of either a less flexible material than that of the body or material that too conforms to the shape of whatever it contacts. When a punctal plug having both a flexible body and a less flexible collarette is inserted into the lacrimal canaliculus, the collarette rests on the exterior of the lacrimal punctum and the body of the punctal plug conforms to the shape of the lacrimal canaliculus. The reservoir and the body of such punctal plugs are preferably coterminous. That is, the reservoir of such punctal plugs preferably make up the entirety of the body, except for the collarette.

In exemplary embodiments in which one or both of a flexible body and collarette are used, the flexible body and flexible collarette can be made of materials that include nylon, polyethylene terephthalate ("PET"), polybutylene terephthalate ("PBT"), polyethylene, polyurethane, silicone, PTFE, PVDF, and polyolefins. Punctal plugs made of nylon, PET, PBT, polyethylene, PVDF, or polyolefins are typically manufactured for example and without limitation, extrusion, injection molding, or thermoforming. Punctal plugs made of latex, polyurethane, silicone, or PTFE are typically manufactured using solution-casting processes.

Processes for manufacturing the punctal plugs useful in the present invention are well known. Typically, the devices are manufactured by injection molding, cast molding, transfer molding or the like. Preferably, the reservoir is filled with one or both of at least one active agent and the active agent-containing material subsequent to the manufacture of the device. Additionally, one or more excipients may be combined with the active agent alone or in combination with the polymeric material.

The amount of active agent used in the devices of the present invention will depend upon the active agent or agents selected, the desired doses to be delivered via the device, the desired release rate, and the melting points of the active agent and active agent-containing material. Preferably, the amount used is a therapeutically effective amount meaning an amount effective to achieve the desired treatment, inhibitory, or prevention effect. Typically, amounts of about 0.05 to about 8,000 micrograms of active agents may be used.

In certain aspects of the present invention, the reservoir may be refilled with a material after substantially all of the active agent-containing material has dissolved or degraded and the active agent is released. For example, the new active agent-containing material can be the same as, or different from, the previous polymeric material, and can contain at least one active agent that is the same as, or different from the previous active agent. Certain punctal plugs used for particular applications can preferably be refilled with a material while the punctal plugs remain inserted in the lacrimal canaliculus, while other punctal plugs are typically removed from the lacrimal canaliculus, a new material is added, and the punctal plugs are then reinserted into the lacrimal canaliculus.

After the device is filled with the active agent, the plug is sterilized by any convenient method including, ethylene oxide, autoclaving, irradiation, and the like and combination thereof. Preferably, sterilization is carried out through gamma radiation or use of ethylene oxide.

The devices described herein may be used to deliver various active agents for the one or more of the treatment, inhibition, and prevention of numerous diseases and disorders. Each device may be used to deliver at least one active agent and can be used to deliver different types of active agents. For example, the devices can be used to deliver azelastine HCl, emadastine difumerate, epinastine HCl, ketotifen fumerate, levocabastine HCl, olopatadine HCl, pheniramine maleate, and antazoline phosphate for one or more of the treatment, inhibition, and prevention of allergies. The devices can be used to deliver mast cell stabilizers, such as, for example, cromolyn sodium, lodoxamide tromethamine, nedocromil sodium, and permirolast potassium.

The devices may be used to deliver mydriatics and cycloplegics including atropine sulfate, homatropine, scopolamine HBr, cyclopentolate HCl, tropicamide, and phenylephrine HCl. The devices can be used to deliver ophthalmic dyes including rose begal, sissamine green, indocyanine green, fluorexon, and fluorescein.

The devices may be used to deliver corticosteroids including dexamethasone sodium phosphate, dexamethasone, fluorometholone, fluorometholone acetate, loteprednol etabonate, prednisolone acetate, prednisolone sodium phosphate, medrysone, rimexolone, and fluocinolone acetonide. The devices may be used to deliver non-steroidal anti-inflammatory agents including flurbiprofen sodium, suprofen, diclofenac sodium, ketorolac tromethamine, cyclosporine, rapamycin methotrexate, azathioprine, and bromocriptine.

The devices may be used to deliver anti-infective agents including tobramycin, moxifloxacin, ofloxacin, gatifloxacin, ciprofloxacin, gentamicin, sulfisoxazolone diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamycin, sulfadiazine, and pyrimethamine.

The devices may be used to deliver agents for the one or more of the treatment, inhibition, and prevention of glaucoma including epinephrines, including, for example: dipivefrin; alpha-2 adrenergic receptors, including, for example, aproclonidine and brimonidine; betablockers including betaxolol, carteolol, levobunolol, metipranolol, and timolol; direct miotics, including, for example, carbachol and pilocarpine; cholinesterase inhibitors, including physostigmine and echothiophate; carbonic anhydrase inhibitors, including, for example, acetazolamide, brinzolamide, dorzolamide, and methazolamide; prostoglandins and prostamides including latanoprost, bimatoprost, uravoprost, and unoprostone cidofovir.

The devices may be used to deliver antiviral agents, including fomivirsen sodium, foscarnet sodium, ganciclovir sodium, valganciclovir HCl, trifluridine, acyclovir, and famciclovir. The devices can be used to deliver local anesthetics, including tetracaine HCl, proparacaine HCl, proparacaine HCl and fluorescein sodium, benoxinate and fluorescein sodium, and benoxnate and fluorexon disodium. The devices may be used to deliver antifungal agents, including, for example, fluconazole, flucytosine, amphotericin B, itraconazole, and ketocaonazole.

The devices may be used to deliver analgesics including acetaminophen and codeine, acetaminophen and hydrocodone, acetaminophen, ketorolac, ibuprofen, and tramadol. The devices may be used to deliver vasoconstrictors including ephedrine hydrochloride, naphazoline hydrochloride, phenylephrine hydrochloride, tetrahydrozoline hydrochloride, and oxymetazoline. Finally, the devices can be used to deliver vitamins, antioxidants, and nutraceuticals including, vitamins A, D, and E, lutein, taurine, glutathione, zeaxanthin, fatty acids and the like.

The active agents delivered by the devices may be formulated to contain excipients including synthetic and natural polymers, including, for example, polyvinylalcohol, polyethyleneglycol, PAA (polyacrylic acid), hydroxymethyl cellulose, glycerine, hypromelos, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids, and sulphobetains.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A lacrimal insert, the lacrimal insert comprising:
a housing including a flange portion, a substantially cylindrical portion, and a diamond shaped cross-section portion, the housing also including at least one opening in fluid communication with a reservoir defined by the housing;
a drug core including one or more therapeutic agents, the drug core being positioned within the reservoir defined by the housing and comprising a substantially cylindrical portion and a diamond-shaped cross-section portion the drug core taking the shape of and filling the reservoir, and making contact with the housing, the substantially cylindrical portions of the housing and the drug core and the diamond shaped cross-section portions of the housing and the drug core being aligned with one another to form a complimentary fit to prevent movement of the drug core relative to the housing; and
a barrier layer affixed to at least one of the housing and the drug core, the barrier layer being configured to inhibit the diffusion of the therapeutic agent through the housing.

2. The lacrimal insert of claim 1 wherein the housing comprises a material selected the following: Polytetrafluoroethylene, Fluorinatedethylenepropylene, Perfluoroalkoxy, Polyvinylidene Fluoride, Tetrafluoroethylene, Hexafluoropropylene and Vinylidene Fluoride, Ethylenetetrafluoroethylene, Chloro Trifluoro Ethylene / Ethylene Copolymer, Polyethylene Terepthalate Polyester, Polyetheretherketone, Nylon 6/6, Nylon 11, Nylon 12, Pebax, Polyethylene, Ultra high molecular weight polyethylene, Ultra low molecular weight polyethylene, High molecular weight polyethylene, High density polyethylene, High density crosslinked polyethylene, Cross-linked polyethylene, Medium density polyethylene, Low density polyethylene, Linear low density polyethylene, Very low density polyethylene, Polypropylene, Polycaprolactone, Cellulose and cellulose derivatives, Cellulose Acetate, Polycarbonate, Cyanoacrylate, Eudragit, Polyimide, Polyamide, Ethylene Vinyl Acetate, Polyurethane, Polysulfone, Polyetherimide, Polytheresulfone, Styrene butadiene Rubber, Polyphenylene Sulfide, Polyphenylene Oxide, Ethylene Propylene Diene Monomer (Rubber), Zeonor, Zeonex, Parylene, Parylene N, Parylene C, Parylene D, Parylene AF-4, Parylene SF, Parylene HT, Parylene A, Parylene AM, Parylene VT-4, Parylene CF, and Parylene X, Polyvinyl alcohol, Polyvinyl acetate, Polyvinyl chloride, Polyisobutylene, Fluro silicones, Liquid curable perfluoropolyether, and Polystyrene.

3. The lacrimal insert of claim 1 wherein the barrier layer comprises a material selected from the following:

Polytetrafluoroethylene, Fluorinatedethylenepropylene, Perfluoroalkoxy, Polyvinylidene Fluoride, Tetrafluoroethylene, Hexafluoropropylene and Vinylidene Fluoride, Ethylenetetrafluoroethylene, Chloro Trifluoro Ethylene / Ethylene Copolymer, Polyethylene Terepthalate Polyester, Polyetheretherketone, Nylon 6/6, Nylon 11, Nylon 12, Pebax, Polyethylene, Ultra high molecular weight polyethylene, Ultra low molecular weight polyethylene, High molecular weight polyethylene, High density polyethylene, High density cross-linked polyethylene, Cross-linked polyethylene, Medium density polyethylene, Low density polyethylene, Linear low density polyethylene, Very low density polyethylene, Polypropylene, Polycaprolactone, Cellulose and cellulose derivatives, Cellulose Acetate, Polycarbonate, Cyanoacrylate, Eudragit, Polyimide, Polyamide, Ethylene Vinyl Acetate, Polyurethane, Polysulfone, Polyetherimide, Polytheresulfone, Styrene butadiene Rubber, Polyphenylene Sulfide, Polyphenylene Oxide, Ethylene Propylene Diene Monomer (Rubber), Zeonor, Zeonex, Parylene, Parylene N, Parylene C, Parylene D, Parylene AF-4, Parylene SF, Parylene HT, Parylene A, Parylene AM, Parylene VT-4, Parylene CF, and Parylene X, Polyvinyl alcohol, Polyvinyl acetate, Polyvinyl chloride, Polyisobutylene, Fluro silicones, Liquid curable perfluoropolyether, and Polystyrene.

\* \* \* \* \*